United States Patent [19]

Umezawa et al.

[11] 4,104,372

[45] Aug. 1, 1978

[54] 1-N-(α-HYDROXY-ω-AMINOALKANOYL) DERIVATIVES OF 3'-DEOXYKANAMYCIN A AND THE PRODUCTION THEREOF

[75] Inventors: Hamao Umezawa; Sumio Umezawa, both of Tokyo; Tsutomu Tsuchiya, Yokohama, all of Japan

[73] Assignee: Zaidan Hojin Biseibutsu Kagaku Kenkyu Kai, Tokyo, Japan

[21] Appl. No.: 678,560

[22] Filed: Apr. 20, 1976

[30] Foreign Application Priority Data

Apr. 24, 1975 [JP] Japan .................................. 50-49105

[51] Int. Cl.$^2$ ........................ A61K 31/71; C07H 15/22
[52] U.S. Cl. ........................ 424/180; 536/10; 536/17
[58] Field of Search .................... 536/10, 17; 424/180, 424/181

[56] References Cited

U.S. PATENT DOCUMENTS

| | | | |
|---|---|---|---|
| 3,904,597 | 9/1975 | Naito et al. | 536/10 |
| 3,929,761 | 12/1975 | Umezawa et al. | 536/10 |
| 3,939,143 | 2/1976 | Umezawa et al. | 536/10 |

*Primary Examiner*—Johnnie R. Brown
*Attorney, Agent, or Firm*—Brady, O'Boyle & Gates

[57] ABSTRACT

1-N-(α-hydroxy-ω-aminoalkanoyl)-derivatives of 3'-deoxykanamycin A or 6'-N-methyl-3'-deoxykanamycin A are provided as new and useful compounds which are active against gram-negative and gram-positive bacteria, including drug-resistant strains of these bacteria. Examples of these compounds include 1-N-((SR)-β-amino-α-hydroxypropionyl)-3'-deoxykanamycin A, 1-N-((S)-γ-amino-α-hydroxybutyryl)-3'-deoxykanamycin A, 1-N-((S)-δ-amino-α-hydroxyvaleryl)-3'-deoxykanamycin A and 1-N-((S)-γ-amino-α-hydroxybutyryl)-6'-N-methyl-3'-deoxykanamycin A. The compounds may be prepared by selective acylation of the 1-amino group of 3'-deoxykanamycin A or 6'-N-methyl-3'-deoxykanamycin A with a corresponding α-hydroxy-ω-amino-alkanoic acid.

7 Claims, No Drawings

1-N-(α-HYDROXY-ω-AMINOALKANOYL) DERIVATIVES OF 3'-DEOXYKANAMYCIN A AND THE PRODUCTION THEREOF

This invention relates to a new semisynthetic antibiotic derivative of kanamycin A, that is, a 1-N-(α-hydroxy-ω-aminoalkanoyl)-3'-deoxykanamycin A or 1-N-(α-hydroxy-ω-aminoalkanoyl)-6'-N-methyl-3'-deoxykanamycin A which is useful for the therapeutic treatment of various infections by gram-negative and gram-positive bacteria, including drug-resistant strains of these bacteria. More particularly, this invention relates to a new kanamycin A derivative which is selected from 1-N-((SR)-β-amino-α-hydroxypropionyl)-3'-deoxykanamycin A, 1-N-((S)-γ-amino-α-hydroxybutyryl)-3'-deoxykanamycin A, 1-N-((S)-δ-amino-α-hydroxyvaleryl)-3'-deoxykanamycin A and 1-N-((S)-γ-amino-α-hydroxybutyryl)-3'-deoxy-6'-N-methylkanamycin A, and a nontoxic pharmaceutically acceptable acid-addition salts thereof. Furthermore, this invention relates to a process for the production of these 1-N-(α-hydroxy-ω-aminoalkanoyl) derivatives of 3'-deoxykanamycin A or a 6'-N-methyl-3'-deoxykanamycin A.

Kanamycins A and B are known aminoglycosidic antibiotics and have widely been used as the chemotherapeutic agent. However, many kanamycin-resistant strains of bacteria have occurred in recent years. For instance, it has been found that some R-factor carrying strains of the gram-negative bacteria, *Staphylococcus aureus* and *Pseudomonas aeruginosa* which have been isolated from patients are resistant to the antibacterial action of kanamycins. The mechanism of resistance of the kanamycin-resistant bacteria to the known aminoglycosidic antibiotics has been studied by H. Umezawa et al. ("Advances in Carbohydrate Chemistry and Biochemistry", Vol. 30, pp. 183–225, 1974, Academic Press). It has been found that some kanamycin-resistant bacteria produce such enzymes capable of phosphorylating the 3'-hydroxyl group of the kanamycins and inactivate the kanamycins with aid of these 3'-phosphotransferases, that some kanamycin-resistant bacteria produce such an enzyme capable of nucleotidylating the 2''-hydroxyl group of the kanamycins and inactivate the kanamycins with aid of the 2''-nucleotidyltransferase, and that another some kanamycin-resistant bacteria produce such enzymes capable of acetylating the 6'-amino group of the kanamycins and inactivate the kanamycins with aid of these 6'-acetyltransferases. In this way, the relationship of the molecular structure of the aminoglycosidic antibiotics to their antibacterial activity, as well as the biochemical mechanism of resistance of the kanamycin-resistant bacteria to the aminoglycosidic antibiotics have been elucidated.

We, the present inventors, have prepared some semisynthetic derivatives of aminoglycosidic antibiotics which are active against various, drug-resistant pathogenic bacteria. Thus, we made our research on the basis of the above findings, and we succeeded in synthetizing 3',4'-dideoxyribostamycin (see the "Journal of Antibiotics" Vol. 25, page 613 (October 1972); 3'-deoxykanamycin A (see U.S. Pat. No. 3,929,761); and 3',4'-dideoxykanamycin B (see U.S. Pat. No. 3,753,973) which are all practically effective against the drug-resistant bacteria capable of producing the 3'-phosphotransferase.

Further, we have found that when a lower alkyl substituent is introduced into the 6'-amino group of kanamycins and their related aminoglycosidic antibiotics, the 6'-N-alkylated derivatives so obtained gain an antibacterial activity which is effective against the drug-resistant bacteria capable of producing the 6'-acetyltransferase. Thus, we succeeded in synthetizing 6'-N-methyl-3',4'-dideoxykanamycin B (see British Pat. No. 1,384,221), as well as 6'-N-methyl-3'-deoxykanamycin B and other 6'-alkyl derivatives of some aminoglycosidic antibiotics (see British Pat. No. 1,426,910) which have been found to be active against various kanamycin-resistant bacteria and *Pseudomonas aeruginosa* (for example, *Pseudomonas aeruginosa* GN 315) capable of producing the 6'-acetyltransferase.

On the other hand, it is known that butirosin B is active against some kanamycin-resistant bacteria and some ribostamycin-resistant bacteria, and that butirosin A and butirosin B are identified as 1-N-((S)-α-hydroxy-γ-amino-n-butyryl)-5-O-β-D-xylofuranosylneamine and 1-N-((S)-α-hydroxy-γ-amino-n-butyryl)-5-O-β-D-ribofuranosylneamine, respectively (see the "Tetrahedron Letters" Vol. 28, pages 2,617 – 2,630 (1971) and German "Offenlegungschrift" No. 1,914,527). Butirosin B, that is, 1-N-((S)-α-hydroxy-γ-amino-n-butyryl)-5-O-β-D-ribofuranosylneamine may also be termed as 1-N-((S)-α-hydroxy-γ-amino-n-butyryl)-ribostamycin. From comparison of the antibacterial activity of butirosin B with that of ribostamycin, we have found that the (S)-α-hydroxy-γ-amino-n-butyryl substituent on the 1-amino group of the butirosin B molecule has an important role in enabling the ribostamycin to be active even against the ribostamycin-resistant bacteria and inhibits the action of the 2''-nucleotidyltransferase.

Utilizing the above finding, we succeeded in synthetizing 1-N-((S)-α-hydroxy-ω-aminoalkanoyl)derivatives of 3',4'-dideoxyribostamycin; 3',4'-dideoxykanamycin B and 6'-N-methyl-3'-deoxykanamycin B, respectively, which are active against the kanamycin-resistant bacteria capable of producing the 2''-nucleotidyltransferase (see British Pat. No. 1,426,908).

We have now made our further research in an attempt to provide as a new and useful compound a new kanamycin derivative which effective not only against the gram-negative and gram-positive bacteria sensitive to the kanamycins but also against the kanamycin-resistant bacteria. As a result, we have now found that selective acylation of the 1-amino group of 3'-deoxykanamycin A or of a 6'-N-methyl-3'-deoxykanamycin A with an α-hydroxy-ω-amino acid gives a new and useful kanamycin A derivative which exhibits broadly a high antibacterial activity against the kanamycin-sensitive bacteria and against the kanamycin-resistant bacteria.

An object of this invention is to provide such new and useful kanamycin A derivatives which exhibit a usefully high antibacterial activity against the kanamycin-sensitive bacteria and against some kanamycin-resistant bacteria and which may be synthetized in a higher yield and are less toxic than the aforesaid 1-N-((S)-α-hydroxy-ω-aminoalkanoyl) derivatives of kanamycin B, 3',4'-dideoxykanamycin B and 6'-N-methyl-3'-deoxykanamycin B. A particular object of this invention is to provide as a new and useful compound a 1-N-(α-hydroxy-ω-aminoalkanoyl) derivative of 3'-deoxykanamycin A or of a 6'-N-methyl-3'-deoxykanamycin A which has the above-mentioned advantageous properties. The other object of this invention is to provide a process for the semisynthetic production of these new kanamycin A derivatives from 3'-deoxykanamycin A or a 6'-N-methyl-3'-deoxykanamycin A which is operable in a facile way and gives the desired product in a favorable yield. Another objects of this invention will be clear from the following descriptions.

According to a first aspect of this invention, therefore, there is provided as a new compound a 1-N-(α-hydroxy-ω-aminoalkanoyl)-3′-deoxykanamycin A or -6′-N-methyl-3′-deoxykanamycin A represented by the formula (I):

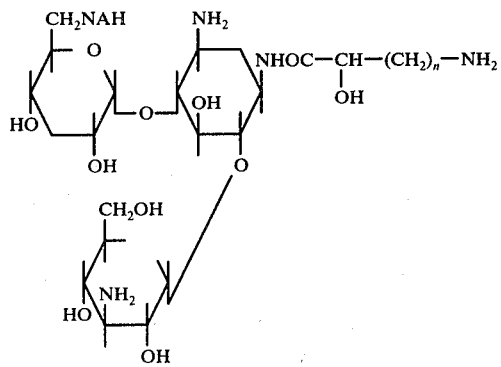

wherein A is a hydrogen atom or methyl group, and n is an integer of 1, 2, 3 or 4, and a pharmaceutically acceptable acid-addition salt thereof.

Examples of the new compound of the above formula (I) are listed below.

(1) 1-N-((SR)-β-amino-α-hydroxypropionyl)-3′-deoxykanamycin A.
(2) 1-N-((S)-γ-amino-α-hydroxybutyryl)-3′-deoxykanamycin A.
(3) 1-N-((S)-δ-amino-α-hydroxyvaleryl)-3′-deoxykanamycin A.
(4) 1-N-((S)-γ-amino-α-hydroxybutyryl)-6′-N-methyl-3′-deoxykanamycin A.

Examples of the pharmaceutically acceptable acid-addition salt of the new compound of the formula (I) according to this invention include a hydrochloride, hydrobromide, sulfate, phosphate, nitrate, carbonate, acetate, maleate, fumarate, succinate, tartarate, oxalate, citrate, methanesulfonate, ethanesulfonate, ascorbate and the like, which may be a mono-, di-, tri- or tetra-salt formed by the interaction of 1 molecule of the new compound of the formula (I) with 1-4 moles of a non-toxic, pharmaceutically acceptable acid. The pharmaceutically acceptable acid includes hydrochloric, hydrobromic, sulfuric, phosphoric, nitric, carbonic, acetic, maleic, fumaric, succinic, tartaric, oxalic, methanesulfonic, ethanesulfonic, ascorbic acid and the like.

The new compounds according to this invention have the following physical, chemical and biological properties:

1-N-((SR)-β-amino-α-hyroxypropionyl)-3′-deoxykanamycin A is a substance in the form of a colorless crystalline powder with an optical rotation $[\alpha]_D^{20} +89°$ (c 1, water). This compound is positive to the ninhydrin reaction.

1-N-((S)-γ-amino-α-hydroxybutyryl)-3′-deoxykanamycin A is a substance in the form of a colorless crystalline powder with an optical rotation $[\alpha]_D^{20} +90°$ (c 1, water). This substance is positive to the ninhydrin reaction.

1-N-((S)-δ-amino-α-hyroxyvaleryl)-3′-deoxykanamycin A is a substance in the form of a colorless crystalline powder with an optical rotation $[\alpha]_D^{20} +87°$ (c 1, water). This substance is positive to the ninhydrin reaction, too.

1-N-((S)-γ-amino-α-hydroxybutyryl)-6′-N-methyl-3′-deoxykanamycin A is a substance in the form of a colorless crystalline powder with an optical rotation $[\alpha]_D^{20} +90°$ (c 1, water). This substance is positive to the ninhydrin reaction.

The minimum inhibitory concentrations (mcg/ml) of the new compounds 1-N-((S)-γ-amino-α-hydroxybutyryl)-3′-deoxykanamycin A (abbreviated as S-AHB-DKA); 1-N-((SR)-β-amino-α-hydroxypropionyl)-3′-deoxykanamycin A (abbreviated as SR-AHP-DKA); 1-N-((S)-δ-amino-α-hydroxyvaleryl)-3′-deoxykanamycin A (abbreviated as S-AHV-DKA); and 1-N-((S)-γ-amino-α-hydroxybutyryl)-6′-N-methyl-3′-deoxykanamycin A (abbreviated as S-AHB-MDKA) against various organisms were determined according to agar dilution-streak method (nutrient agar) at 37° C, the estimation being made after 18 hours incubation. For the comparison purpose, the minimum inhibitory concentrations (mcg/ml) of the parent antibiotic 3′-deoxykanamycin A, as well as 1-N-((S)-γ-amino-α-hydroxybutyryl)kanamycin A (abbreviated as AHB-KMA) which is known from U.S. Pat. No. 3,781,268 were also determined in the same manner as stated above.

The antibacterial spectra of the concerned compounds are shown in Table 1 below.

Table 1

Antibacterial spectra of 1-N-(α-hydroxy-ω-aminoalkanoyl) derivatives of 3′-deoxykanamycin A and 6′-N-methyl-3′-deoxykanamycin A

| Test Organisms | Minimum Inhibitory Concentrations (mcg/ml) | | | | | |
| --- | --- | --- | --- | --- | --- | --- |
| | S-AHB-DKA | SR-AHP-DKA | S-AHV-DKA | S-AHB-MDKA | DKA* | AHB-KMA* |
| *Staphylococcus aureus* FDA 209P | 0.39 | 0.78 | 0.78 | 0.78 | 1.56 | 0.78 |
| *Escherichia coli* K-12 | 0.39 | 0.39 | 0.78 | 0.39 | 3.12 | 0.78 |
| *Escherichia coli* K-12 ML 1629 | 0.39 | 0.78 | 1.56 | 1.56 | 3.12 | 0.78 |
| *Escherichia coli* K-12 ML 1630 | 0.78 | 0.78 | 1.56 | 0.78 | 3.12 | 1.56 |
| *Escherichia coli* K-12 ML 1410 | 0.39 | 0.78 | 3.12 | 0.78 | 3.12 | 0.78 |
| *Escherichia coli* K-12 LA 290 R55 | 0.78 | 1.56 | 3.12 | 1.56 | 3.12 | 0.78 |
| *Escherichia coli* K-12 W677 | <0.2 | 0.78 | 3.12 | 3.12 | 3.12 | 0.78 |
| *Escherichia coli* K-12 JR66/W677 | 0.78 | 1.56 | 3.12 | 1.56 | >100 | 3.12 |
| *Pseudomonas aeruginosa* A3 | 3.12 | 3.12 | 3.12 | 3.12 | 3.12 | 3.12 |
| *Pseudomonas aeruginosa* No. 12 | 3.12 | 6.25 | 6.25 | 3.12 | 12.5 | 6.25 |
| *Pseudomonas aeruginosa* GN315 | 100 | >100 | >100 | 6.25 | >100 | 100 |

*Comparative

The new compound of the aforesaid formula (I) according this invention is of low toxicity to animals including men, as it shows an $LD_{50}$ value of more than 200 mg/kg upon intravenous injection of the compound in mice. 1-N-((S)-γ-amino-α-hydroxybutyryl)-3′-deoxykanamycin A exhibits a particularly lower $LD_{50}$ value of more than 250 mg/kg upon intravenous injection in mice. This is to be compared to the fact that the known 1-N-(α-hydroxy-ω-aminoalkanoyl) derivatives of 3',4'-dideoxykanamycin B and 6'-N-methyl-3'-deoxykanamycin B have an $LD_{50}$ value of less than 200 mg/kg upon intravenous injection of these compound in mice. In addition, the new compound of the aforesaid formula (I) according to this invention broadly exhibits a high antibacterial activity against various gram-negative and gram-positive bacteria sensitive to kanamycins, as well as against the kanamycin-resistant strains thereof as stated hereinbefore, and the antibacterial activity is enhanced in comparison to a compound having 3'-hydroxyl group such as 1-N-((S)-γ-amino-α-hydroxybutyryl)-kanamycin A (AHB-KMA). Moreover, the lack of the 3'-hydroxyl group of the new compound will prevent the future possible occurrence of resistant-bacteria for the new compound during the clinical use thereof, thus ensuring that the new compound is therapeutically effective for long years. Therefore, the new compound of this invention may be useful in therapeutic treatment of infections by various gram-negative and gram-positive bacteria.

The compound of this invention may be administered orally, intraperitoneally, intravenously, subcutaneously or intramuscularly using any pharmaceutical form known to the art for such administration and in a similar manner to kanamycins. For instance, the compound of the formula (I) of this invention may be administered orally using any pharmaceutical form known to the art for such oral administration. Examples of pharmaceutical forms for oral administration are powders, capsules, tablets, syrup, and the like. Suitable dose of the compound for the effective treatment of bacterial infections is in a range of 0.25 – 2 g per person a day when it is given orally. It is preferred that said dose should be orally administered in three to four aliquots per day. The compound of this invention may also be administered by intramuscular injection at a dosage of 50 – 500 mg per person in two to four times per day. Moreover, the new compound of the invention may be formulated into an ointment for external application which contains the compound of this invention at a concentration of 0.5 – 5% by weight in mixture with a known ointment base such as polyethylene glycol. Moreover, the new compound of this invention is useful to sterilize surgeric instruments when the sterilization is accompanied by adequate mechanical cleansing.

In principle, the new compound of the formula (I) according to this invention may be prepared from a starting compound, 3'-deoxykanamycin A or a 6'-N-methyl-3'-deoxykanamycin A represented by the formula (II):

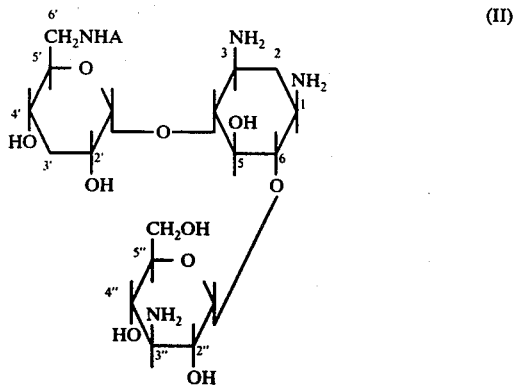

wherein A is a hydrogen atom or methyl group, by acylating selectively the 1-amino group of the starting compound (II) with an α-hydroxy-ω-amino acid of the formula (III):

$$H_2N-(CH_2)_n-CH(OH)-COOH \qquad (III)$$

wherein n is an integer of 1, 2, 3 or 4, in a manner known per se in the prior art of acylating amino group in the conventional synthesis of peptides. The 3'-deoxykanamycin A compound according to the formula (II) in which A is hydrogen atom contains four, free amino groups (that is, the 1-, 3-, 6'- and 3''-amino groups). While, the 6'-N-methyl-3'-deoxykanamycin A compound according to the formula (II) in which A is methyl group contains three, free amino groups (that is, 1-, 3- and 3''-amino groups) and one methylamino group (at the 6'-position) per molecule thereof. In order to achieve the production of the 1-N-(α-hydroxy-ω-aminoalkanoyl)-3'-deoxykanamycin A or -6'-methyl-3'-deoxykanamycin A of the formula (I) according to this invention, it is required that only the 1-amino group of the compound (II) should be selectively acylated with the α-hydroxy-ω-amino acid (III) without involving the acylation of the other amino groups, and occasionally the 6'-methylamino group if the latter is present. It will be obvious that the new compound (I) as desired would be obtained in a best yield, if the α-hydroxy-ω-amino acid reactant (III) is reacted with such an amino-protected derivative derived from the 3'-deoxykanamycin A compound (II) in which all of the free amino groups other than the 1-amino group have been blocked by a known amino-protecting group with only the 1-amino group remaining free. Preparation of such amino-protected derivative is possible only with needing a very complicated method comprising a number of reaction steps for the preparation. In this situation, it is rather preferred to prepare such an amino-protected derivative of the 3'-deoxykanamycin compound (II) in which only the 6'-amino group or the 6'-methylamino group has been blocked by the amino-protecting group while the other amino groups remain in the free state. This is because the preparation of the latter type of the amino-protected derivative of the 3'-deoxykanamycin A compound (II) is relatively easier and simpler owing to the fact that the 6'-amino group or 6'-methylamino are most highly reactive among the amino groups of the compound (II) and hence can be blocked preferentially by the amino-protecting group with keeping the other amino groups unblocked.

When such type of the amino-protected derivative of the 3'-deoxykanamycin A compound (II) in which the 6'-amino group or 6'-methylamino group has been blocked is reacted with the α-hydroxy-ω-amino acid reactant (III) of which the ω-amino group may preferably be blocked by an amino-protecting group, there is formed mixed reaction products comprising the desired 1-N-mono-acylated derivative of the 3'-deoxykanamycin A compound in which only the 1-amino group has been acylated with the α-hydroxy-ω-amino acid reactant (III), together with such undesired mono- and poly-N-acylated derivatives in which one or more of the amino groups other than the 1-amino group has or have been acylated with the α-hydroxy-ω-amino acid (III), respectively. Thus, the acylation products resulted from the above acylation reaction are actually obtained in the form of a mixture of differently N-acylated derivatives including the desired 1-N-mono-acylated derivative. If desired, it is possible to isolate the desired 1-N-monoacylated derivative from the mixed N-acylated derivatives by subjecting to a chromatographic method. However, the mixed N-acylated derivatives may directly be treated for the removal of the amino-protecting groups therefrom, when there is produced a mixture of the desired 1-N-mono-acylated product of the formula (I) with the otherwise mono- and poly-N-acylated, undesired by-products derived from the compound (II). The desired product (I) may be isolated from the undesired by-products by subjecting the mixture of them to a chromatographic method.

According to a second aspect of this invention, therefore, there is provided a process for the production of the new compound of the aforesaid formula (I), which comprises acylating selectively the 1-amino group of 3'-deoxykanamycin A, a 6'-N-methyl-3'-deoxykanamycin A or an amino-protected derivative thereof, that is, a 3'-deoxykanamycin A compound represented by the formula (IV):

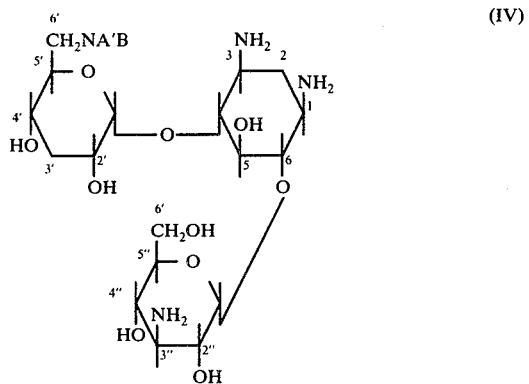

wherein A' is a hydrogen atom, methyl group or a known mono-valent amino-protecting group, B is a hydrogen atom or a known mono-valent amino-protecting group, or A' and B taken together form a known di-valent amino-protecting group, with an α-hydroxy-ω-amino acid of the formula (V):

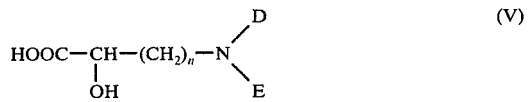

wherein $n$ is an integer of 1, 2, 3, or 4, D is a hydrogen atom or a known mono-valent amino-protecting group, E is a hydrogen atom or a known mono-valent amino-protecting group, or D and E taken together form a known di-valent amino-protecting group, or with a functional derivative of said amino acid, to produce as a reaction product a 1-N-acylated derivative of the formula (VI):

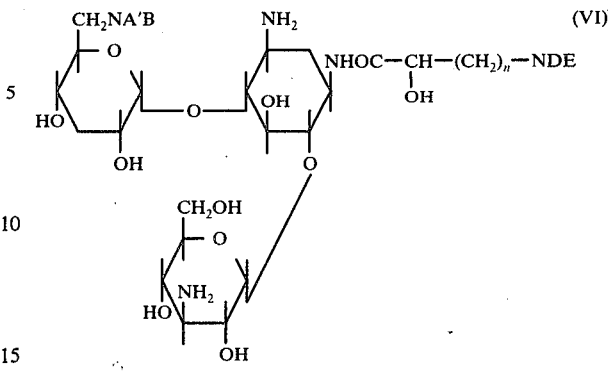

wherein A', B, D, E and $n$ are as defined above, and then removing the remaining amino-protecting groups from said 1-N-acylated derivative (VI) to produce the desired compound of the formula (I). This process according to the second aspect of this invention may be followed by the step of isolating the desired compound of the formula (I) by a chromatographic method from the undesired otherwise mono- or poly-N-acylated derivatives by-produced.

In the 3'-deoxykanamycin A compound of the general formula (IV) which is employed as the starting material in the process of this invention, it is possible that both of A' and B are each a hydrogen atom. It is possible that A' is a hydrogen atom and B is a known mono-valent amino-protecting group. It is also possible that both of A' and B are each a mono-valent amino-protecting group. Occasionally, A' and B taken together may form a known di-valent amino-protecting group. As suitable examples of the known mono-valent amino-protecting group for A' and B which are available in this invention, there may be mentioned an acyl group, particularly an alkanoyl group such as acetyl and an aroyl group such as benzoyl; an alkoxycarbonyl group, particularly an alkoxycarbonyl group of 2–6 carbon atoms; an aralkoxycarbonyl group; an aryloxycarbonyl group; an arylsulfonyl group; an alkylsulfonyl group; an aralkylsulfonyl group; trityl group; an enamine group (that is, a group of the formula

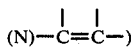

such as dimedone typically, and a trialkylsilyl group.

Particularly, the mono-valent amino-protecting group of the acyl type may be, for example, acetyl and o-nitrophenylacetyl. The alkoxycarbonyl group which is available as the mono-valent amino-protecting group may be, for example, t-butoxycarbonyl and t-amyloxycarbonyl. The aralkoxycarbonyl group which is suitable as the amino-protecting group may be benzyloxycarbonyl and p-nitrobenzyloxycarbonyl, for example. The aryloxycarbonyl group may be, for example, phenoxycarbonyl and p-methoxyphenoxycarbonyl. The alkylsulfonyl group which is available as the mono-valent amino-protecting group may preferably be a lower alkylsulfonyl of which the alkyl is of 1-4 carbon atoms, for example, methylsulfonyl and ethylsulfonyl. The arylsulfonyl group may be p-toluenesulfonyl, for example. The aralkylsulfonyl group may be, for example, benzylsulfonyl. The enamine group which is available as the amino-protecting group may be dimedone radical. The trialkylsillyl group which is suitable as the amino-protecting group may be trimethylsillyl and triethylsillyl, for example.

When a pair of the groups A' and B taken together form a di-valent amino-protecting group, this di-valent amino-protecting group may be phthaloyl or may generally be an alkylidene or arylidene group of the formula =CHX in which X is an alkyl group, particularly an alkyl group of 1–6 carbon atoms or X is an aryl group such as phenyl, tolyl, p-methoxyphenyl or o-hydroxyphenyl. Suitable examples of the alkylidene group may be isopropylidene. Suitable examples of the arylidene group may be benzylidene.

In the 3'-deoxykanamycin A compound of the formula (IV) which is employed as the starting material in the second aspect process of this invention, the group A' may either be a hydrogen atom or methyl group.

In the amino acid of the formula (V) which is employed as the acylating reactant in the present process, the group R is hydroxyl, and the groups D and E may each be a hydrogen atom. When the groups D and E are the amino-protecting groups, these may be the same as those given for the aforesaid groups A' and B of the starting 3'-deoxykanamycin A compound (IV). When any of the groups D and E is a mono-valent amino-protecting group, it may preferably be an acyl group, including an alkanoyl group of 2–5 carbon atoms and an aroyl group such as benzoyl; an alkyloxycarbonyl group; an aralkyloxycarbonyl group; an aryloxycarbonyl group; an alkylsulfonyl group or an arylsulfonyl group. When the groups D and E taken together form a known di-valent amino-protecting group, it may preferably be an alkylidene group or an arylidene group. Suitable examples of the mono-valent amino-protecting groups D and E may be acetyl or o-nitrophenylacetyl. The alkoxycarbonyl group which is available as the amino-protecting groups D and E may be, for example, t-butoxycarbonyl and t-amyloxycarbonyl. The aralkyloxycarbonyl group may be benzyloxycarbonyl and p-nitrobenzyloxycarbonyl. The aryloxycarbonyl group may be, for example, phenoxycarbonyl and p-methoxyphenoxycarbonyl. The alkylsulfonyl group which is suitable for the amino-protecting groups D and E may be an lower alkylsulfonyl group such as methylsulfonyl and ethylsulfonyl. The arylsulfonyl group may be p-toluenesulfonyl, for example. The aralkylsulfonyl group may be, for example, benzylsulfonyl.

When the groups D and E taken together form a known di-valent amino-protecting group, it may preferably be an alkylidene or arylidene group of the formula =CHY in which Y is an alkyl group or an aryl group. The alkyl group for Y may be methyl, ethyl, propyl and butyl, and the aryl group for Y may be phenyl, p-methoxyphenyl, p-chlorophenyl and p-nitrophenyl.

The α-hydroxy-ω-amino acid compound (V) employed in the present process may either be in the form of racemic form or in the optically active forms such as the L-isomer and the D-isomer. It is preferred, however, that α-hydroxy-γ-aminobutyric acid which is a compound of the formula (V) where $n$ is 2, and α-hydroxy-δ-aminovaleric acid which is a compound of the formula (V) where $n$ is 3 should be in the form of the optically active L-isomer, as the final product derived therefrom exhibits a higher antibacterial activity than the final product derived from the D-isomer.

In the acylation step of the process according to this invention, the 3'-deoxykanamycin A compound (IV) is reacted with the α-hydroxy-ω-amino acid reactant (V)

in a manner known in the conventional preparation of amides. Thus, the 3'-deoxykanamycin A compound (IV) may be reacted with the acylating reagent (V) in solution in tetrahydrofuran, dioxane, ethyleneglycol dimethylether, dimethylformamide, dimethylacetamide, propyleneglycol dimethylether or a mixture thereof at a temperature of up to 50° C and preferably of up to 25° C and in the presence of a dehydrating agent such as dicyclohexylcarbodiimide. Of course, the α-hydroxy-ω-amino acid reactant (V) may also be employed in the form of its functionally equivalent, reactive derivative such as an acid chloride, a mixed acid anhydride, an active esters or an azide derivative thereof. For instance, the α-hydroxy-ω-amino acid reactant (V) may firstly be reacted with N-hydroxysucciimide in the presence of dicyclohexylcarbodiimide as the dehydrating agent to prepare its active ester of the formula:

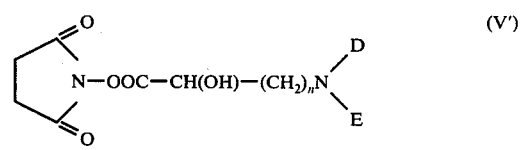

which is, in turn, reacted with the starting 3'-deoxykanamycin A compound (IV) for the N-acylation of the latter compound. It is preferred that the 3'-deoxykanamycin A compound (IV) should be reacted with a 0.5 to 3 molar proportion and preferably a 0.5 to 1.5 molar proportion of the active ester form of the α-hydroxy-amino acid compound (V') in a mixed solvent consisting of water and an organic solvent such as tetrahydrofuran.

In the acylating step of the present process, there is produced the mixed N-acylated derivatives of the 3'-deoxykanamycin A compound (IV) which are usually in the form of a mixture of the desired 1-N-monoacylated derivative and the undesired otherwise mono-N-acylated derivative as well as the undesired poly-N-acylated derivatives. The mixed N-acylated derivatives so produced may then directly be treated so as to remove the remaining amino-protecting groups therefrom, that is to say, to convert the remaining amino-protecting groups into hydrogen atoms, respectively.

The removal of the remaining amino-protecting groups from the above-mentioned mixed N-acylated derivatives which are produced by the acylation step of the present process may be effected in the following different ways known per se. Thus, when the amino-protecting group A', B, D, E is of an acyl group or an alkyloxycarbonyl group, such as t-butoxycarbonyl, an cycloalkyloxycarbonyl group, aryloxycarbonyl group, an alkylidene or arylidene group or trityl group, the removal of this kind of the amino-protecting group may be effected by subjecting the mixed N-acylated derivatives to a mild hydrolysis treatment with an alkali or with an acid such as aqueous trifluoroacetic acid, aqueous acetic acid and diluted hydrochloric acid. When the amino-protecting groups is of an aralkyloxycarbonyl group such as benzyloxycarbonyl, the removal of this sort of the amino-protecting group may be effected by subjecting the mixed N-acylated derivatives to a hydrogenolysis treatment in the presence of a palladium catalyst, a platinum catalyst, Raney nickel, rhodium catalyst, luthenium catalyst or a nickel catalyst. Palladium-carbon catalyst is preferred for this purpose. The o- nitrophenoxyacetyl group as the amino-protecting group may be removed by a reductive treatment. When the amino-protecting group is phthaloyl group, the removal of phthaloyl group may be achieved by treating the mixed N-acylated derivatives with hydrazine hydrate in ethanol. The reaction for the removal of the above-mentioned kinds of the amino-protecting group may generally be conducted in water or a mixed solvent of water and a water-miscible organic solvent such as dioxane, tetrahydrofuran, ethyleneglycol dimethylether, and propyleneglycol dimethylether. The above hydrogenolysis treatment may be carried out at a temperature of 0–100° C and for a reaction time of 0.5–48 hours using hydrogen gas at a pressure of 1–5 atms. The removal of the amino-protecting group of the alkyl-, aralkyl- or aryl-sulfonyl type may preferably be effected by treating with sodium in liquid ammonia, but it may generally be accomplished in a known manner by photolysis, by a treatment with radicals or by a treatment with a metal in liquid ammonia. With the N-acylated derivatives contain different kinds of the amino-protecting groups, the N-acylated derivatives may be subjected to simultaneous or successive different treatments adapted to remove the different amino-protecting groups therefrom.

The removal of the remaining amino-protecting groups gives a mixture of the differently N-acylated products derived from 3'-deoxykanamycin A compound (II) which comprises the desired final product, 1-N-(α-hydroxy-ω-aminoalkanoyl)-3'-deoxykanamycin A or -6'-N-methyl-3'-deoxykanamycin A(I), its position-isomers and the poly-N-acylated products, together with the unreacted 3'-deoxykanamycin A material (IV). The isolation of the desired final product (I) may efficiently be achieved by subjecting said mixture to a column chromatography using, for example, silica gel or a cation-exchange resin having carboxylic functions, such as Amberlite IRC 50 or Amberlite CG 50 (a product of Rohm & Haas, Co., U.S.A.), a weak cation-exchanger such as CM-Sephadex C-25 (a product of Pharmacia Co., Sweden) or CM-cellulose. The eluate from the chromatographic process is collected in fractions, and the antibacterial activity of these fractions is detected using the sensitive bacteria and resistant bacteria as the test microorganisms. Through this detection of the antibacterial activity of each fraction, it is ready to find out the active fractions containing the desired compound (I). A portion was taken out of these active fractions and subjected to a thin layer chromatography with silica gel using, for example, a solvent system of butanol-ethanolchloroform-17% aqueous ammonia. In this way, it is possible to find out such fractions which give a single spot at the specific Rf value of the desired compound (I) and hence contain solely the desired product (I). Such fractions may be combined together and concentrated to dryness under reduced pressure to recover the desired compound (I).

With respect to a case where appropriate amino-protecting group is used for the groups A', B, D and E of the 3'-deoxykanamycin A compound (IV) and the amino acid reactant (V), there is provided according to a particular embodiment of the second aspect of this invention a process for the production of a 1-N-(α-hydroxy-ω-aminoalkanoyl)-3'-deoxykanamycin A or -6'-N-methyl-3'-deoxykanamycin A of the formula (Ia)

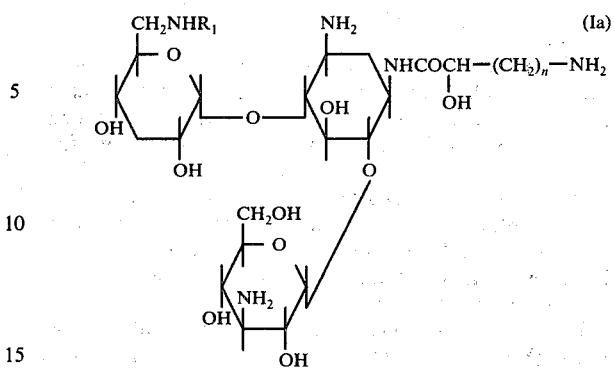

wherein $R_1$ is a hydrogen atom or methyl group, and $n$ is a whole number of 1, 2, 3 or 4, which comprises acylating selectively the 1-amino group of a 3'-deoxy kanamycin A compound of the formula (IVa)

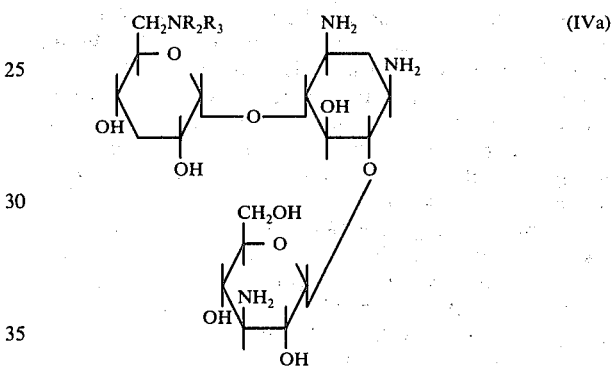

wherein $R_2$ and $R_3$ may be the same or different and are each a hydrogen atom or an acyl group, an alkoxycarbonyl group, an aralkyloxycarbonyl group, an aryloxycarbonyl group, an arylsulfonyl group, an alkylsulfonyl group, an arylsulfonyl group, trityl group, an enamine group typically represented by dimedone group, or a trialkylsillyl group, or $R_2$ and $R_3$ taken together form an alkylidene or arylidene group of the formula $=CHX$ where X is an alkyl group or an aryl group; or of the formula (IVb)

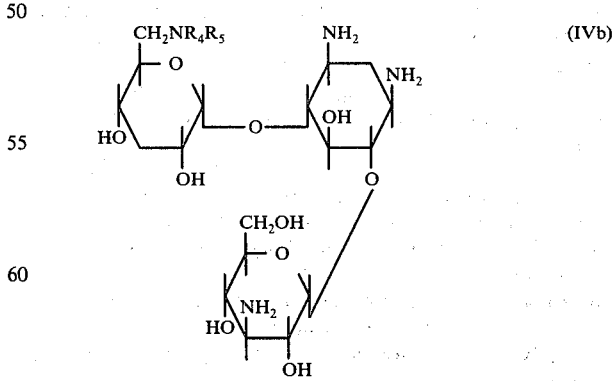

wherein $R_4$ is methyl and $R_5$ has the same meaning as $R_2$ given in the formula (IVa), with an α-hydroxy-ω-amino acid of the formula (Va)

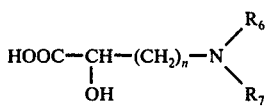

wherein $R_6$ and $R_7$ are each a hydrogen atom, an acyl group, an alkoxycarbonyl group, an aralkyloxycarbonyl group or an aryloxycarbonyl group; and $n$ is a whole number of 1, 2, 3 or 4; or of the formula (Vb)

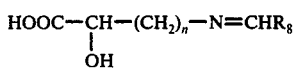

wherein $R_8$ is a hydrogen atom, an alkyl group or an aryl group, and $n$ is a whole number of 1, 2, 3 or 4, or with a functional derivative of said α-hydroxy-ω-amino acid (Va) or (Vb) to produce the 1-N-monoacylated product of the 3'-deoxykanamycin A compound (IVa) or (IVb), and then removing the remaining amino-protecting groups from said 1-N-mono-acylated product to give the desired compound of the formula (I a), and finally isolating the desired compound (Ia) by a chromatographic method.

A 6'-N-methyl-3'-deoxykanamycin A which is one of the starting compound (IV) for use in the process of this invention may be prepared by 6'-N-methylating 3'-deoxykanamycin A (see U.S. Pat. No. 3,929,761) according to known various methylation methods. For instance, 6'-N-methyl-3'-deoxykanamycin A may be prepared by the 6'-N-methylation method set forth in British Pat. No. 1,426,910 specification.

A 6'-N-protected derivative of 3'-deoxykanamycin A or of 6'-N-methyl-3'-deoxykanamycin A of the formula (II), that is, such a 3'-deoxykanamycin A compound of the formula (IV) containing an amino-protecting group as the group A' which is one of the starting compound for use in the process of this invention may be prepared by reacting 3'-deoxykanamycin A or 6'-N-methyl-b 3'-deoxykanamycin A (II) with a reagent which is conventionally used in the prior art of the polypeptide synthesis to introduce the amino-protecting group. The reagent which is used to introduce the amino-protecting group may be of various known types and may be those as shown in British Pat. No. 1,426,908 specification. The preparation of the 3'-deoxykanamycin A compound (IV) in the form of its 6'-N-protected derivative may be achieved in the same manner as detailed in the British Pat. No. 1,426,908 specification for the preparation of the 6'-N-protected derivatives of the 3',4'-dideoxyribostamycin or 3',4'-dideoxykanamycin B.

For instance, 6'-N-benzyloxycarbonyl-3'-deoxykanamycin A which is corresponding to a 3'-deoxykanamycin A compound of the formula (IV) where the group A' is hydrogen atom and the group B is benzyloxycarbonyl group may be prepared by the following method: 3'-Deoxykanamycin A is dissolved in a solvent which may be water, dimethylformamide, dimethylacetamide, dioxane, methanol, ethanol, acetone, pyridine, an N-alkylpyridine, tetrahydrofuran or a mixture thereof and may preferably be a mixture of water and tetrahydrofuran. The solution of 3'-deoxykanamycin A so obtained is admixed with an amount of benzyl p-nitrophenyl carbonate, and the mixture is agitated for 1-15 hours at a temperature of −10° C to 10° C for the benzyloxylation. After this reaction, the reaction solution is adsorbed on an cationexchange resin Amberlite IRC-50 (H cycle) which is subsequently washed with water-dioxane (1:1 by volume). The resin having the active product adsorbed therein is then eluted with water-dioxane containing 0 to 0.2N ammonia, and the eluate is collected in fractions. Such fractions of the eluate which are positive to the reaction with ninhydrin are combined together, and concentrated to dryness to give a solid product comprising 6'-N-benzyloxycarbonyl-3'-deoxykanamycin A.

The new compound of the formula (I) according to this invention is useful to treat therapeutically the bacterial infections as stated hereinbefore. According to a third aspect of this invention, therefore, there is provided a pharmaceutical composition for treating bacterial infections in living animals, including man, which comprises an antibacterially effective dosage of a 1-N-(α-hydroxy-ω-aminoalkanoyl)-3'-deoxykanamycin A compound of the aforesaid formula (I) or the pharmaceutically acceptable acid-addition salt thereof as the active ingredient, in combination with a pharmaceutically acceptable carrier for the active ingredient.

This invention is now illustrated with reference to the following Examples to which this invention is not limited in any way.

EXAMPLE 1

Synthesis of 1-N-((S)-γ-amino-α-hydroxybutyryl)-3'-deoxykanamycin A [a compound of the formula (1) were $n = 2$]

(a) A solution of 20 mg of 3'-deoxykanamycin A in 1 ml. of water-tetrahydrofuran (1:2 by volume) was admixed with a solution of N-hydroxysuccinimide ester of (S)-α-hydroxy-γ-phthalimidobutyric acid which was prepared previously by interacting 20 mg of (S)-α-hydroxy-γ-phthalimideobutyric acid, 9 mg of N-hydroxysuccinimide and 20 mg of dicyclohexylcarbodiimide (a dehydrating agent) in anhydrous tetrahydrofuran. The whole admixture was agitated and left to stand at 0° C overnight for the acylation. The precipitate deposited was removed from the reaction mixture by filtration, and the remaining solution (the filtrate) was concentrated to dryness to give a solid containing 1-N-((S)-α-hydroxy-γ-phthalimidobutyryl)-3'-deoxykanamycin A.

(b) The solid so obtained was dissolved in 0.6 ml. of water, and the resulting aqueous solution was admixed with hydrazine hydrate (60 mg), followed by heating at 60° C for 2 hours to effect the removal of the phthaloyl group. The reaction mixture was cooled to ambient temperature and filtered. The filtrate so obtained was passed through a column of a strongly basic anion-exchange resin, Amberlite IRA 400 (OH cycle) (a product of Rohm & Haas Co., U.S.A.), which was subsequently eluted with water. The eluate was collected in 0.5 ml. fractions, and each fraction was detected for its positive reaction with ninhydrin and for its antibacterial activity to a kanamycin-resistance strain, *Escherichia coli* JR66/W677. Such fractions which were remarkably positive to the ninhydrin reaction and also remarkably active to said kanamycin-resistant strain were combined together and concentrated to dryness. The resulting solid residue was dissolved in a volume of water, and the aqueous solution obtained was passed through a column of a weak cation-exchanger, CM-Sephadex C-25 (a product of Pharmacia Co., Sweden). This cation-exchanger column was then eluted with 0 to 0.3N aqueous ammonia while increasing gradually the concentration of ammonia in the eluent. The eluate was collected in 0.5 ml. fractions, and every fraction was again detected for its positive reaction with ninhydrin and for its antibacterial activity to the kanamycin-resistant strain, *Escherichia coli* JR66/W677. Such fractions which were strongly positive to the ninhydrin reaction and also strongly active to said kanamycin-resistant strain were combined together and concentrated to dryness, affording a solid in the form of a colorless crystalline powder. This solid was identified as 1-N-((S)-γ-amino-α-hydroxybutyryl)-3'-deoxykanamycin A. Yield 1.1 mg. $[\alpha]_D^{20}$ +90° (c 1, water).

Elemental analysis Calcd. for $C_{22}H_{43}N_5O_{12}\cdot H_2CO_3\cdot H_2O$: C 42.52, H 7.29, N 10.78% Found: C 42.78, H 7.31, N 10.51%

EXAMPLE 2

Synthesis of 1-N-((S)-δ-amino-α-hydroxyvaleryl)-3'-deoxykanamycin A [a compound of the formula (1) were n=3]

The process of Example 1 was repeated using 11 mg of (S)-α-hydroxy-δ-phthalimidovaleric acid in place of he (S)-α-hydroxy-γ-phthalimidobutyric acid. The above titled compound was obtained as a colorless crystalline powder in a yield of 0.8 mg. $[\alpha]_D^{20}$ +87° (c 1, water).

EXAMPLE 3

Synthesis of 1-N-((SR)-β-amino-α-hydroxypropionyl)-3'-deoxykanamycin A [a compound of the formula (I) where n=1]

The process of Example 1 was repeated using 10 mg of (SR)-α-hydroxy-β-phthalimidopropionic acid in place of the (S)-α-hydroxy-β-phthalimidobutyric acid. The above titled compound was obtained as a colorless crystalline powder in a yield of 0.8 mg. $[\alpha]_D^{20}$ +89° (c 1, water).

Elemental analysis Calcd. for $C_{21}H_{41}N_5O_{12}\cdot H_2CO_3\cdot H_2O$: C 41.56, H 7.14, N 11.02% Found: C 41.19, H 7.38, N 10.86%

EXAMPLE 4

Syntheis of 1-N-((S)-γ-amino-α-hydroxybutyryl)-3'-deoxykanamycin A.

(a) A solution of 10 mg of 3'-deoxykanamycin A in 0.5 ml. of water-dioxane (1:2 by volume) was admixed with 20 mg of benzyl p-nitrophenyl carbonate ($C_6H_5CH_2OCO_2C_6H_4$-p-$NO_2$), and the admixture was agitated at 0° C for 6 hours for the reaction. The reaction mixture was passed through a column of a cation-exchange resin, Amberlite IRC 50 (H cycle) (a product of Rhom & Haas Co., U.S.A.), nd this resin column was then washed with water-dioxane (1:1 by volume) and subsequently eluted with water-dioxane (1:1 by volume) containing ammonia (at an $NH_3$ concentration of 0 to 0.2 N). The eluate was collected in 0.5 ml. fractions, and such fractions which were positive to the ninhydrin reaction were combined together and concentrated to dryness. The solid residue so obtained was found to be the mixed reaction products mainly comprising the 6'-N-protected derivative of 3'-deoxykanamycin A, that is, 6'-N-benzyloxycarbonyl-3'-deoxykanamycin A.

(b) The above solid residue was dissolved in 0.5 ml. of water-tetrahydrofuran (1:2 by volume), and the resulting solution was admixed with a solution of N-hydroxysuccinimide ester of (S)-α-hydroxy-γ-phthalimidobutyric acid which was prepared previously by interacting 10 mg of (S)-α-hydroxy-γ-phthalimidobutyric acid, 4.5 mg of N-hydroxysuccinimide and 10 mg of dicyclohexylcarbodiimide in anhydrous tetrahydrofuran. The whole admixture was agitated and allowed to stand at 0° C overnight for the acylation. The precipitate deposited was removed from the reaction mixture by filtration, and the remaining solution (the filtrate) was concentrated to dryness to give a solid residue comprising 1-N-((S)-α-hydroxy-γ-phthalimidobutyryl)-6'-N-benzyloxycarbonyl-3'-deoxykanamycin A.

(c) The solid residue so obtained was dissolved in 0.4 ml. of aqueous methanol, to which was then added hydrazine hydrate (30 mg). The mixture was heated at 60° C for 1.5 hours to effect the removal of the phthaloyl group. The reaction mixture was cooled to ambient temperature and filtered. The filtrate was passed through a column of an anion-exchange resin, Amberlite IRA 400 (OH cycle), and this resin column was then eluted with aqueous methanol. The eluate was collected in fractions, and such fractions which were positive to the ninhydrin reaction were combined together and concentrated to dryness. The solid so obtained was dissolved in a volume of water-dioxane (1:1 by volume) and was then subjected to hydrogenolysis with hydrogen in the presence of palladium-black catalyst to effect the removal of the benzyloxycarbonyl group. The reaction mixture was filtered to remove solid matters, and the filtrate was concentrated. The syrupy material so obtained was dissolved in a volume of water, and this aqueous solution was passed through a column of a weak cation-exchanger, CM-Sephadex C-25. This column was then developed with 0 to 0.3N aqueous ammonia while increasing gradually the $NH_3$ concentration. The eluate was collected in 0.5 ml. fractions, and every fraction was detected for its positive reaction with ninhydrin and for its antibacterial activity to a kanamycin-resistant strain, *Escherichia coli* JR66/W677. Such fractions which were strongly positive to the ninhydrin reaction and also strongly active against said kanamycin-resistant strain were combined together and concentrated to dryness. There was obtained a substance which was confirmed as a compound identical to the final product of Example 1(b). Yield 2.8 mg.

EXAMPLE 5

Synthesis of 1-N-((SR)-β-amino-α-hydroxypropionyl)-3'-deoxykanamycin A

The process of Example 4 was repeated using 10 mg of (SR)-α-hydroxy-β-phthalimidopropionic acid instead of the (S)-α-hydroxy-γ-phthalimidiobutyric acid. There was obtained the above titled compound which was entirely the same as the final product of Example 3. Yield 2.3 mg.

EXAMPLE 6

Synthesis of 1-N-((S)-γ-amino-α-hydroxybutyryl)-6'-N-methyl-3'-deoxykanamycin A [a compound of the formula (I) where A is methyl and n is 2]

A solution of 10 mg of 6'-N-methyl-3'-deoxykanamycin A in 0.5 ml. of water-dioxane (1:2 by volume) was admixed with 20 mg of benzyl p-nitrophenyl carbonate. The admixture was agitated at 0° C for 6 hours for the benzylation. The reaction mixture so obtained was subsequently processed in the same manner as in Example 4(a), to give a solid residue containing 6'-N-benzyloxycarbonyl-6'-N-methyl-3'-deoxykanamycin A. This solid residue was then processed in the same manner as in Example 4(b) and (c) to afford the above titled compound in the form of a colorless crystalline powder. Yield 2.0 mg. $[\alpha]_D^{20}$ +90° (c 1, water).

Elemental analysis Calcd. for $C_{23}H_{45}N_5O_{12} \cdot H_2CO_3 \cdot H_2O$: C 43.43, H 7.44, N 10.55% Found: C 43.13, H 7.80, N 10.46%

What we claim is:

1. A compound of the formula (I):-

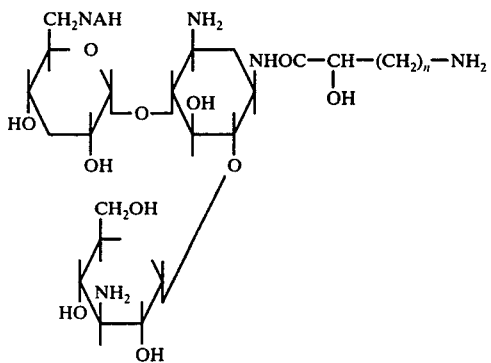

wherein A is a hydrogen atom or methyl group, and n is an integer of 1, 2, 3 or 4, or a pharmaceutically acceptable acid-addition salt thereof.

2. A compound according to claim 1 which is selected from 1-N-((SR)-β-amino-α-hydroxypropionyl)-3'-deoxykanamycin A, 1-N-((S)-γ-amino-α-hydroxybutyryl)-3'-deoxykanamycin A, 1-N-((S)-δ-amino-α-hydroxyvaleryl)-3'-deoxykanamycin A, 1-N-((S)-γ-amino-α-hydroxybutyryl)-6'-N-methyl-3'-deoxykanamycin A, and a pharmaceutically acceptable acid-addition salt thereof.

3. A pharmaceutical composition for treating infections in living animals, including man, caused by gram-negative and gram-positive bacteria, which comprises an antibacterially effective dosage of the compound of the formula (I) according to claim 1 or a pharmaceutically acceptable acid-addition salt thereof as the active ingredient, in combination with a pharmaceutically acceptable carrier for the active ingredient.

4. 1-N-((S)-γ-amino-α-hydroxybutyryl)-3'-deoxykanamycin A or a pharmaceutically acceptable acid-addition salt thereof.

5. 1-N-((S)-γ-amino-α-hydroxybutyryl)-6'-N-methyl-3'-deoxykanamycin A or a pharmaceutically acceptable acid-addition salt thereof.

6. 1-N-((S)-δ-amino-α-hydroxyvaleryl)-3'-deoxykanamycin A or a pharmaceutically acceptable acid-addition salt thereof.

7. A pharmaceutical composition for treating infections in living animals, including man, caused by gram-negative and gram-positive bacteria, which comprises an anti-bacterially effective dosage of 1-N-((S)-γ-amino-α-hydroxybutyryl)-3'-deoxykanamycin A or a pharmaceutically acceptable acid-addition salt thereof as the active ingredient, in combination with a pharmaceutically acceptable carrier for the active ingredient.

* * * * *